United States Patent [19]

Daniels

[11] Patent Number: 4,728,553

[45] Date of Patent: Mar. 1, 1988

[54] PRISONER LEG RESTRAINT

[76] Inventor: Jerry Daniels, 4308 Ooltewah-Ringgold Rd., Ooltewah, Tenn. 37363

[21] Appl. No.: 2,212

[22] Filed: Jan. 12, 1987

Related U.S. Application Data

[63] Continuation-in-part of Ser. No. 803,650, Dec. 2, 1985, Pat. No. 4,643,932.

[51] Int. Cl.$^4$ .................. A62B 35/00; B60R 22/00
[52] U.S. Cl. .................................. 428/100; 128/134; 297/466
[58] Field of Search ............... 428/100; 297/466, 468, 297/474; 128/134

[56] References Cited

U.S. PATENT DOCUMENTS

| | | | |
|---|---|---|---|
| 3,307,872 | 3/1967 | Murcott | 297/468 |
| 3,529,865 | 9/1970 | Atwell | 428/181 X |
| 3,939,829 | 2/1976 | Spann | 128/133 |
| 3,992,057 | 11/1976 | Studebaker | 297/468 X |
| 4,004,583 | 1/1977 | Johnson | 297/466 X |
| 4,117,840 | 10/1978 | Rasure | 128/134 |
| 4,173,974 | 11/1979 | Belliveau | 128/133 |
| 4,359,200 | 11/1982 | Brevard et al. | 297/216 X |
| 4,360,014 | 11/1982 | Manahan | 128/134 |
| 4,488,316 | 12/1984 | Mosca | 428/100 X |
| 4,595,618 | 6/1986 | Caringer | 428/100 |
| 4,643,932 | 2/1987 | Daniels | 428/100 |
| 4,672,910 | 6/1987 | Cook | 150/52 K X |

Primary Examiner—Henry F. Epstein
Attorney, Agent, or Firm—Alan Ruderman

[57] ABSTRACT

A system for restraining the lower limbs of a prisoner being conveyed in a vehicle, such as a police car, to preclude injury to persons and to property by violent kicking action of the prisoner. The system utilizes a laminated strap having synthetic hook and loop fastening elements formed on one ply of the laminate and a reinforced vinyl backing formed on the other ply. One end of the strap is fastened to a grommet through which the other end of the strap may be drawn and folded over so that hook elements and loop elements may be engaged to adhere while the vinyl portion of the strap is tightly engaged about the lower limbs of the prisoner. A belt having a hook including a biased latch at one end of the belt is attached to the strap at the other end, and the hook can be secured to an anchor on the floor of the vehicle. The attachment of the belt to the strap may be either by a fixed securement or by an adjustable connection.

14 Claims, 5 Drawing Figures

U.S. Patent  Mar. 1, 1988  4,728,553
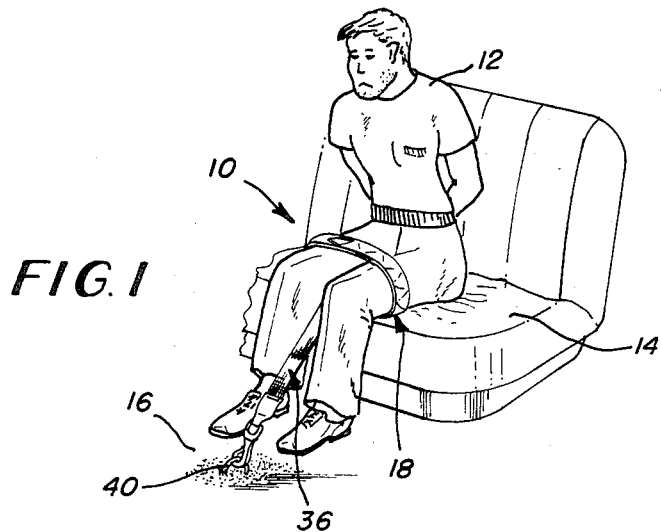
FIG. 1
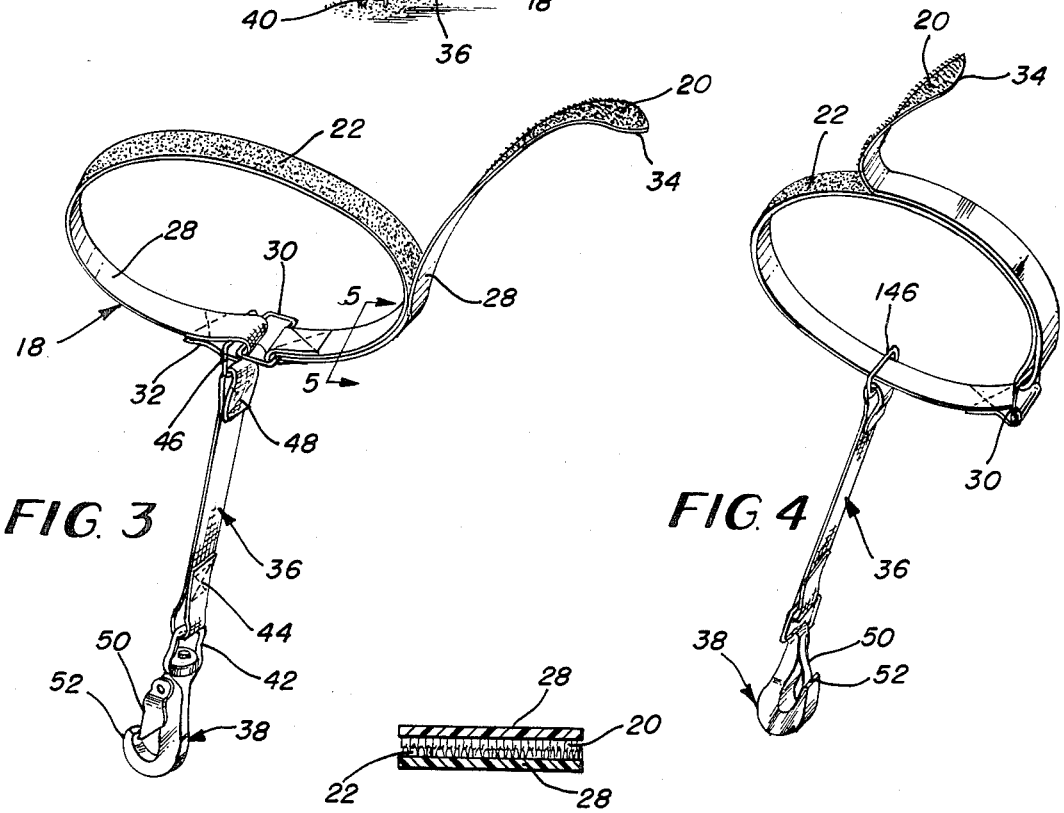
FIG. 3
FIG. 4
FIG. 5
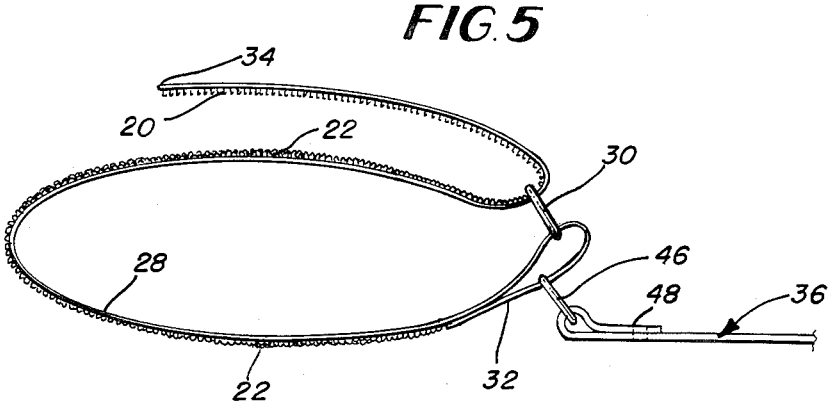
FIG. 2

PRISONER LEG RESTRAINT

REFERENCE TO RELATED APPLICATIONS

This application is a continuation in part of copending application Ser. No. 06/803,650 filed Dec. 2, 1985, now U.S. Pat. No. 4,643,932, dated Feb. 17, 1987.

BACKGROUND OF THE INVENTION

This invention relates to the restraint of the lower limbs of a prisoner to a support surface and more particularly to a belting system utilizing a laminated fastening strap for encircling the lower limbs of a prisoner, the belting having connecting means for attachment to a floor or the like and the laminated strap having synthetic material fastening elements which rapidly adhere when pushed together, the fastening elements being laminated to a backing of sufficient strength to restrain the limbs of a violent prisoner.

It is well known in the law enforcement field that substantial physical injury to an arresting officer and physical damage to public property has resulted when a suspect being taken prisoner resists arrest. It is notoriously well known to restrain the hands and arms of the prisoner by handcuffs or the like connecting the prisoner's hands together, in front of or behind his or her body. However, although the legs of the prisoner are powerful weapons, especially when the prisoner is emotionally charged, no leg restraining system has been developed which functions satisfactorily. Thus, there are many cases in which an arresting officer has been kicked violently as the prisoner is placed into a police cruiser, and also many more documented cases wherein the police cruiser or squad car has been badly battered by a prisoner's feet and legs as the prisoner is being driven to the station house or other detention center. In certain cases the entire partition between the police officer and the prisoner has been shattered, although most damage occurs to the doors, side panels and windows.

The use of shackles or chains to restrain the legs and feet of a prisoner is useful once a prisoner has been subdued, but such leg manacles cannot be readily placed on the prisoner and are not practical for use by an arresting officer. Moreover, unless heavily weighted they would not prevent the prisoner from lashing out with his or her feet.

Because of numerous instances in which police officers and public property have been damaged, violently acting prisoners have been restrained by other means resulting in charges of "police brutality" and, of course, costly litigation and negative publicity.

SUMMARY OF THE INVENTION

Consequently, it is a primary object of the present invention to provide restraining means for the lower limbs of a prisoner taken into custody by law enforcement officials, the restraining means being rapidly and securely attached about the prisoner and readily secured to a fixed support such as the floor of a police car.

It is another object of the present invention to provide the flexible belting including a laminated fastening strap which can securely and rapidly encircle and restrain the lower limbs such as the legs, thighs or ankles of a prisoner taken into police custody, the belting including means for rapidly connecting the strap to a relatively fixed surface, such as the floor of a police cruiser or the like, to preclude violent kicking and thrashing of the prisoner's feet.

It is a further object of the present invention to provide lower limb restraining means for resisting prisoners being conveyed to a detention center such as a station house or the like, the restraining means comprising a laminated strap having synthetic loop and fastener elements extending from a surface thereof and bonded to a strong plastic sheet of material such as reinforced vinyl, the strap being secured adjacent one end to a grommet through which the other end may be directed after encircling the lower limbs of the prisoner so that one type of fastener element may be superposed over and rapidly connected to fastener elements of the other type on the adjacent portion of the strap, the outer surfaces of the plastic sheet facing the limbs of the prisoner, and a second grommet carried by the strap for attaching one end of belting having a biased connecting latch at the other end, the latch being adapted to be connected to an anchor fixed to the floor of the conveyor.

Accordingly, the present invention provides a restraining belt means for the lower limbs of a prisoner or the like, the belt means comprising a laminated strap of the type forming the subject matter of the aforesaid copending application Ser. No. 06/803,650 now U.S. Pat. No. 4,643,932 having first and second plies of material bonded together, the first ply having interconnectable plastic hook and loop fastener elements such as that sold under the trademark VELCRO bonded to a second ply of a strong pliable sheet of material such as reinforced vinyl. The hook and loop fastener elements extend from one surface of the strap so that one set of the elements may be folded back onto and adhere to the other set of elements when pressed together. One end of the strap is secured to a grommet or the like through which the other or free end of the strap may be drawn with the outer surface of the second ply folded upon itself in superposed relationship with the limbs of the prisoner therebetween. The free end of the strap may then be looped over the grommet for engaging one set of the fastener elements with the other set. One end of additional belt means is carried by the strap in either fixed relationship thereto or adjustable thereon preferably by means of a second grommet or the like, the other end of the additional belt means having a latch adapted for rapid attachment to an anchor fixed to a support to which the prisoner is to be restrained.

Thus, a law enforcement officer after restraining the arms of a prisoner by handcuffs or the like may restrain the legs of the prisoner by looping the strap about the legs or thighs and rapidly pressing the VELCRO fastener elements together, thereafter attaching the latch to the anchor.

This system has been highly successful and has drawn accolades from police officers during initial tests. It is expected that bodily injury and property damages will be substantially reduced when taking violent persons into lawful custody.

BRIEF DESCRIPTION OF THE DRAWINGS

The particular features and advantages of the invention as well as other objects will become apparent from the following description taken in connection with the accompanying drawings, in which:

FIG. 1 is a perspective view depicting a prisoner having his lower limbs restrained by restraining belt means constructed in accordance with the principles of the present invention;

FIG. 2 is an elevational view of the restraining belt means of FIG. 1 with portions thereof broken away;

FIG. 3 is a perspective view of restraining belt means constructed in accordance with the principles of the present invention, wherein the anchor attaching belting is fixedly secured to the strap;

FIG. 4 is a view similar to FIG. 2 illustrating a second embodiment in which the anchor attaching belt means is adjustably disposed along the strap means; and FIG. 5 is a cross sectional view taken substantially along FIG. 5—5 of FIG. 3.

DESCRIPTION OF THE PREFERRED EMBODIMENT

Referring now to the drawings and particularly to FIG. 1, the restraining system 10 of the present invention is illustrated as applied to a prisoner 12 in lawful custody seated on a seat of an official vehicle while being conveyed to a police station or the like, the vehicle having a floor 16. As conventional with regard to those disposed to violence, the arms of the prisoner are handcuffed behind his back. Conventionally, the prisoner's lower limbs, such as his legs, are free and, if the prisoner is emotionally charged and highly violent, his feet can do great personal and physical damage. In some instances to minimize injuries the prisoner's shoes are removed. However, even if that can be accomplished by a single arresting officer without injury, for those prisoners trained in the martial arts even this is of minimal value. Thus, there has been a great need to provide law enforcement officials with the means for restraining the lower limbs of a prisoner when believed necessary. Such a restraining means must be easily and readily applied by an officer in the field and in the heat of making an arrest.

As illustrated in the drawings, the present invention provides a lower limb restraining means comprising a strap 18 formed from a laminate as described in the aforesaid U.S. application Ser. No. 803,650. On one surface of the laminate there are synthetic hook and loop fastener elements such as is known in the trade as "VELCRO" or similar material comprising a plastic sheet having a myriad of closely spaced synthetic plastic hooks 20 and loops 22 which when pushed or squeezed together interlock to form a strong connection which resist separation by a pull in the plane of the interacting parts, but which may be pulled apart by a separating pull on an end of one of the parts at an angle to the plane. A substantial longitudinally extending portion of the fastening surface of the strap preferably has the hook elements while the remainder of the strap carries the loop elements. The other surface of the laminate comprises a backing 28 preferably formed from reinforced vinyl, which is bonded along one surface to the rear surface of the hook and loop fastener elements, preferably along the borders of the strap, and preferably also at selected locations transverse to the borders, as described in the aforesaid U.S. patent application. Thus, a strap comprising two plies is provided wherein one of the plies comprises the "VELCRO" extending from a surface thereof and the other ply comprising a reinforced vinyl sheet, the reinforced vinyl and the bond between the two plies forming an extremely strong strap. The strap may be of any convenient length, and it has been found that a strap of approximately 45 inches in length has worked well for its intended purpose, and the length of the portion of the strap having the loops 22 was approximately 30 inches with the hooks 20 comprising the remainder of the strap. Moreover, the strap may comprise a single length or may be formed from two laminated strips secured together, one of the strips having the hooks and the other having the loops.

As illustrated in the various figures of the drawing, one end of the strap is looped about a grommet 30, folded back upon itself for a short distance as illustrated at 32 and secured to the superposed portion of the strap over which it is folded. The grommet preferably is a metal ring or any similar type member through which the strap may be drawn. Securement may be by stitching or the like. Although either the hook or the loop end of the strap may be attached to the grommet 30 as aforesaid, the preferred end is that which carries the loop 22, as illustrated. The free end 34, i.e., the end remote from the grommet 30, may then be drawn through the grommet and folded back such that the loops 22 are disposed in facing relationship with a portion of the hooks 20. Thus, the free end 34 of the strap is folded so that the vinyl surface of the ply at the loop end faces the vinyl surface at the grommet end of the strap. The free end of the strap may thus be drawn through the grommet and folded over the grommet so that the interlinking hook and loop fastening elements of the "VELCRO" can be secured together. Accordingly, the strap may be encircled about the legs or thighs of a prisoner with only portions of the vinyl abutting the prisoner.

A second strap 36 having a hook member 38 secured adjacent one end thereof may be connected to the strap 18 at the other end, and the hook 38 secured to an anchor 40 on the floor of the vehicle or the like. The strap 36 may be of conventional belting or webbing such as utilized for automobile or airplane safety seat belts formed from woven nylon. One end of the belt 36 may thus be drawn through a ring 42 connected to the hook member 38 and folded back and sewn to the major portion of the belt 36 as illustrated at 44. The other end of the belt may either be fixedly or adjustably attached to the strap 18. For example, in FIG. 3 a second grommet 46 may be secured within the same loop of the strap 18 which secures the grommet 30, i.e., the lap 32 formed at the end of the strap remote from the free end 34. The belting 36 may then pass through the grommet 46 and be secured by stitching between the lap 48 and the adjacent superposed portion of the belt 36. With this construction the belt 36 and the hook 38 is always attached to the strap 18. In some instances it may be preferred that the belt 36 be adjustably attached to the strap 18. To this end, FIG. 4 illustrates that the belt 36 may be secured about a grommet 146 at the end remote from the hook 38 in the same manner as the belt 36 in FIG. 3 is fastened about the grommet 46, but the grommet 146 is not permanently attached to the strap 18 but is free to move therealong.

The hook 38, in both the embodiments illustrated in FIGS. 3 and 4, includes a resiliently biased latch member 50 which can be readily squeezed to overcome the bias and open the free end 52 of the hook so that it may receive or release the anchor 40, the bias being applied to urge the latch against the end 52 of the hook.

In use, after the prisoner is handcuffed, the strap 18 may be applied about his legs or thighs prior to or as he enters the vehicle. The hook 38 may then be secured to the anchor 40 thereby to restrain the prisoner from violently kicking his feet.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. Apparatus for restraining the lower limbs of a prisoner or the like to an anchor fixed to a support surface, said apparatus comprising an elongated laminated strap having first and second plies of material bonded together, the first ply comprising a plastic sheet having hook and loop fastener elements extending from a surface thereof, the hooks extending from a location on said sheet toward one end and the loops extending from proximate said location toward the other end, said second ply comprising a vinyl sheet of the same size as said first ply, a grommet fastened to one of said ends of said strap, the second of said ends being a free end, said grommet being of a size for receiving said free end of said strap and permitting said free end to be drawn therethrough and folded over said grommet with portions of said hook and loop elements disposed in facing relationship so as to cooperatively adhere together when engaged, whereby said strap may be adjustably disposed about the lower limbs of said prisoner to lock said limbs together, and a belt of finite length having a first end connected to said strap and having hook means secured at another end, said hook means having latch means for rapid attaching to said anchor.

2. Apparatus as recited in claim 1, wherein said belt is fixedly attached to said strap.

3. Apparatus as recited in claim 2, including a second grommet fastened to said one of said ends, and said belt is fastened to said second grommet.

4. Apparatus as recited in claim 1, wherein said belt is adjustably disposed on said strap.

5. Apparatus as recited in claim 4, including a second grommet disposed about said strap for movement therealong, and said belt is fastened to said second grommet.

6. Apparatus as recited in claim 1, wherein said latch means is resiliently biased to close said hook means.

7. Apparatus as recited in claim 1, wherein said anchor is secured to the floor of a vehicle.

8. Apparatus for restraining the lower limbs of a prisoner or the like to a vehicle whithin which the prisoner is confined, said apparatus comprising an elongated laminated strap having first and second plies of material bonded together, the first ply comprising a plastic sheet having hook and loop fastener elements extending from a surface thereof, the hooks extending from a location on said sheet toward one end and the loops extending from proximate said location toward the other end, said second ply comprising a vinyl sheet of the same size as said first ply, a grommet fastened to one of said ends of said strap, the second of said ends being a free end, said grommet being of a size for receiving said free end of said strap and permitting said free end to be drawn therethrough and folded over said grommet with portions of said hook and loop elements disposed in facing relationship so as to cooperatively adhere together when engaged, whereby said strap may be adjustably disposed about the lower limbs of said prisoner to lock said limbs together, and a belt of finite length having a first end connected to said strap and having securing means fastened at another end for rapid attachment to said vehicle.

9. Apparatus as recited in claim 8, wherein said belt is fixedly attached to said strap.

10. Apparatus as recited in claim 9, including a second grommet fastened to said one of said ends, and said belt is fastened to said second grommet.

11. Apparatus as recited in claim 8, wherein said belt is adjustably disposed on said strap.

12. Apparatus as recited in claim 11, including a second grommet disposed about said strap for movement therealong, and said belt is fastened to said second grommet.

13. Apparatus as recited in claim 8, wherein said securing means is a hook means having latch means resiliently biased to close said hook means.

14. Apparatus as recited in claim 8, wherein an anchor is secured to the floor of a vehicle.

* * * * *